(12) United States Patent
Desi Reddy et al.

(10) Patent No.: US 10,370,365 B2
(45) Date of Patent: Aug. 6, 2019

(54) PROCESS FOR THE PREPARATION OF CANAGLIFLOZIN

(71) Applicant: OPTIMUS DRUGS (P) LIMITED, Hyderabad (IN)

(72) Inventors: Srinivas Reddy Desi Reddy, Hyderabad (IN); Dnyandev Ragho Rane, Hyderabad (IN); Venkata Srinivasa Rao Velivela, Hyderabad (IN)

(73) Assignee: OPTIMUS DRUGS (P) LIMITED, Hyderabad (IN)

( * ) Notice: Subject to any disclaimer, the term of this patent is extended or adjusted under 35 U.S.C. 154(b) by 80 days.

(21) Appl. No.: 15/244,766

(22) Filed: Aug. 23, 2016

(65) Prior Publication Data
US 2017/0073336 A1 Mar. 16, 2017

Related U.S. Application Data

(63) Continuation of application No. PCT/IB2016/050080, filed on Jan. 8, 2016.

(30) Foreign Application Priority Data

Sep. 16, 2015 (IN) .......................... 4950/CHE/2015

(51) Int. Cl.
*C07D 409/10* (2006.01)
*C07D 333/16* (2006.01)

(52) U.S. Cl.
CPC ......... *C07D 409/10* (2013.01); *C07D 333/16* (2013.01)

(58) Field of Classification Search
CPC .......................... C07D 409/10; C07D 333/16
See application file for complete search history.

(56) References Cited

U.S. PATENT DOCUMENTS 7,943,788 B2  5/2011  Nomura et al.

FOREIGN PATENT DOCUMENTS

| CN | 103980263 A | 8/2014 | |
|---|---|---|---|
| WO | WO-2005/012326 A1 | 2/2005 | |
| WO | WO-2013/064909 A2 | 5/2013 | |
| WO | WO-2013/068850 A2 | 5/2013 | |
| WO | WO-2016098016 A1 * | 6/2016 | ........... C07D 333/22 |

OTHER PUBLICATIONS

WIPO Publication of in 6343/CHE/2014 filed Dec. 17, 2014, published Jun. 23, 2016. (Year: 2016).*
Lemaire et al., Org. Lett., 2012, 14(6), p. 1480-1483. (Year: 2012).*
Kraus et al., J. Org. Chem., 1998, 53, p. 752-753. (Year: 1998).*
Eckert, T.S., J. Chem. Educ., 1987, 64(2), p. 179. (Year: 1987).*
International Search Report for PCT/IB2016/050080 dated Jun. 15, 2016.
Written Opinion for PCT/IB2016/050080 dated Jun. 15, 2016.

* cited by examiner

*Primary Examiner* — Jonathan S Lau
(74) *Attorney, Agent, or Firm* — Blank Rome LLP

(57) ABSTRACT

The present invention provides a novel process for the preparation of Canagliflozin (I) and its hydrates thereof by employing novel intermediates. The present invention is also provides commercially and industrial applicable process.

6 Claims, No Drawings

PROCESS FOR THE PREPARATION OF CANAGLIFLOZIN

This application is a continuation of International Patent Application No. PCT/IB2016/050080, filed Jan. 8, 2016, and claims the benefit of Indian Patent Application No. 4950/CHE/2015, filed Sep. 16, 2015, both of which are hereby incorporated by reference.

FIELD OF THE INVENTION

The present invention provides a novel process for the preparation of Canagliflozin (I) and its hydrates thereof by employing novel intermediates. The present invention is also provides commercially and industrial applicable process.

BACKGROUND OF THE INVENTION 1-(β-D-glucopyranosyl)-4-methyl-3-[5-(4-fluorophenyl)-2-thienylmethyl]benzene, hemihydrate also known as Canagliflozin, belongs to a novel therapeutic class of sodium-glucose co-transporter 2 inhibitors. US drug regulatory approval was received in March 2013 (INVOKANA™) for Canagliflozin as an adjunct to diet and exercise to improve glycemic control in adults with type-2 diabetes mellitus, where it is represented by the following general formula (I):

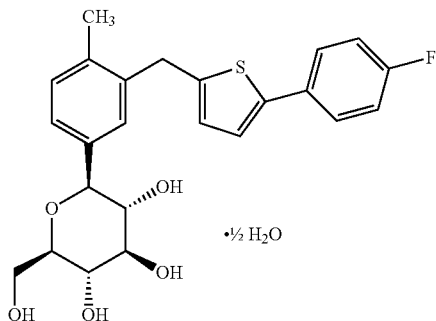

U.S. Pat. No. 7,943,788 B2 first discloses Canagliflozin and its process for the preparation thereof, by reacting 2-(4-fluorophenyl)thiophene (II) is condensed with 5-bromo-2-methylbenzoic acid (III) to produce (5-bromo-2-methylphenyl)[5-(4-fluorophenyl)thiophen-2-yl]methanone of formula (IV), which is reduced to produce 2-(5-bromo-2-methylbenzyl)-5-(4-fluorophenyl)thiophene (V), further condensed with 2,3,4,6-tetrakis-O-trimethylsilyl-D-gluconolactone (VI) in presence of base to produce α-D-glucopyranose, 1-C-[3-[[5-(4-fluorophenyl)-2-thienyl]methyl]-4-methylphenyl]-2,3,4,6-tetrakis-O-(trimethylsilyl)- of formula (VII). The compound of formula (VII) is deprotected in presence of acid and further reduced to produce Canagliflozin.

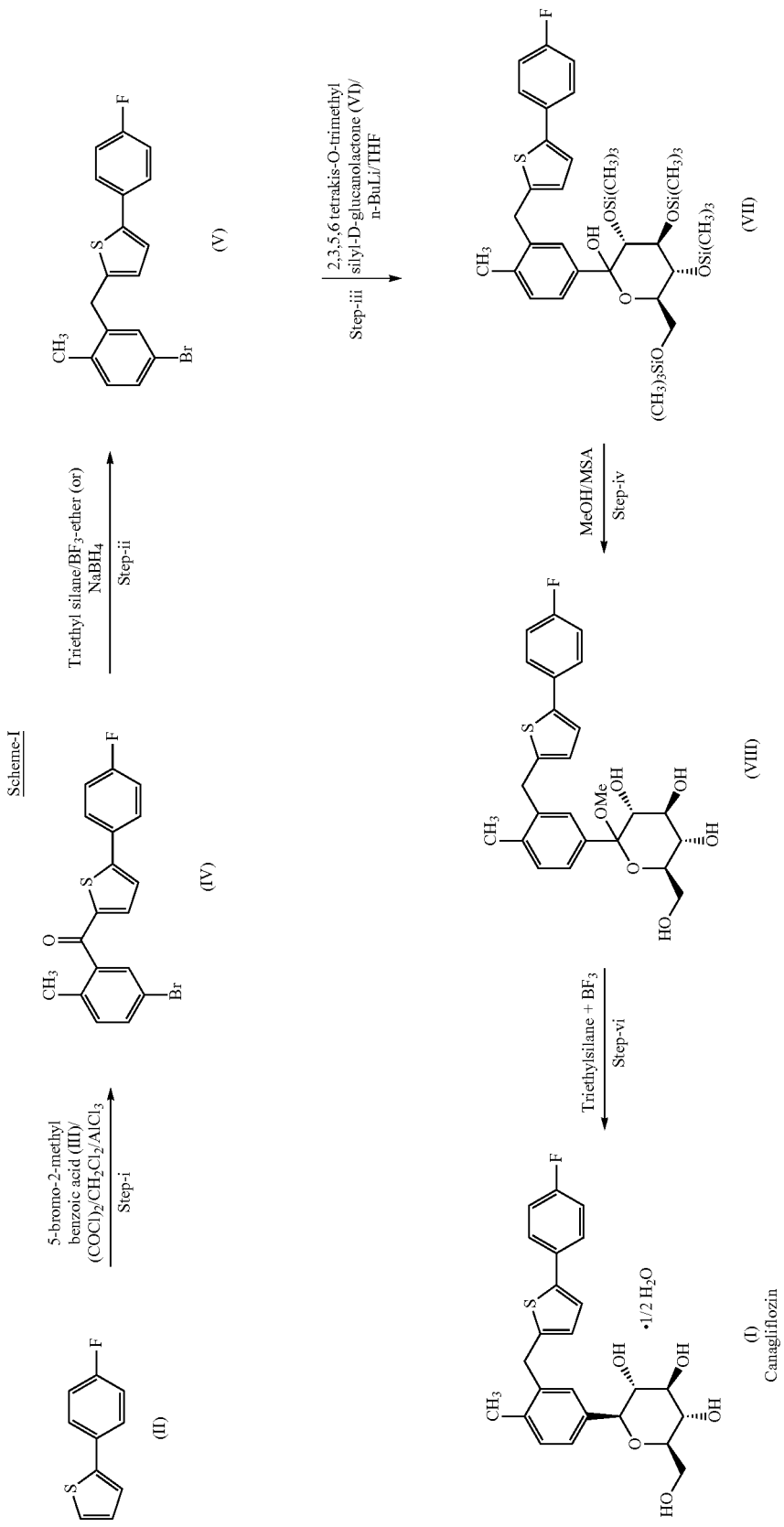
Scheme-I

CN 103980263 discloses a process for the preparation of Canagliflozin of formula (I), by reacting 2-methylbenzoic acid (IX) with iodine in presence of $Fe_2O_3/HIO_4$ to produce 5-iodo-2-methylbenzoic acid (X), the compound of formula (X) is converted acid chloride of formula (XI) in presence of thionyl chloride, the compound of formula (IX) is condensed with 2-(p-fluoro phenyl)-thiophene (II) to produce-(5-Iodo-2-methylbenzyl)-5-(4-fluorophenyl)thiophene (XII), followed by condensation with formula (XIII) to produce the compound of formula (XIV), deprotection of compound of formula (XIV) to produce Canagliflozin (I).

Hence, there is consequently a need for a novel method for the preparation of Canagliflozin and its intermediates. The above disadvantages are overcome by the present invention provides an industrial viable process for the preparation of Canagliflozin (I) and this method is simple and efficient, wide-ranging sources of raw materials, synthetic route is simple, easy operation, mild reaction conditions, the desired reaction time is short, high yield with low synthesis cost, easy post-processing, eco-friendly and suitable for industrial production.

Scheme-II

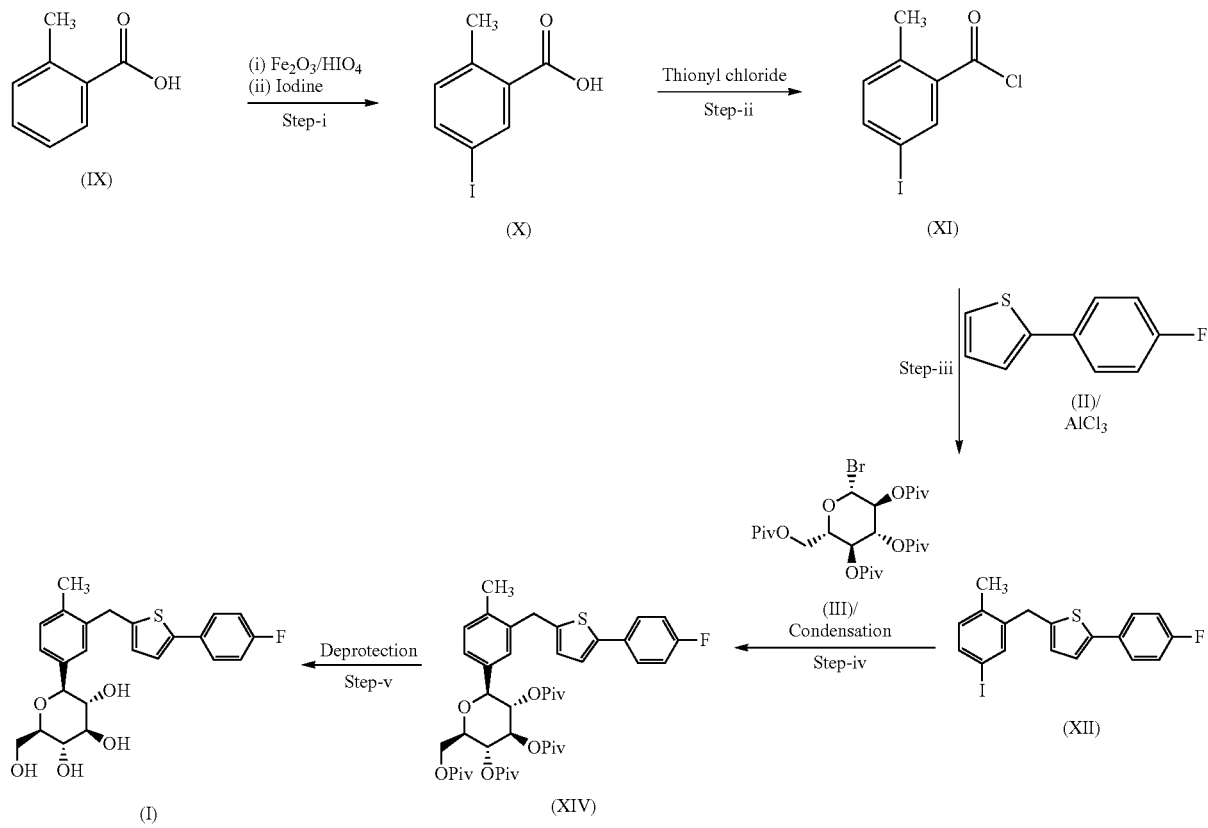

WO 2013/068850 discloses redox economic processes for preparing C-arylglucosides that can be useful as drugs, including SGLT2 inhibitors, prodrugs or synthetic building blocks. The particular focus of the present process for, but not limited to, the manufacture of SGLT2 inhibitors. The glucoside may be in the D- or L-configuration.

WO 2013/064909 A3 discloses a novel crystalline complexes and amorphous forms of SGLT2 inhibitors, and processes for the preparation of these forms. These crystalline complexes of SGLT2 inhibitors are designated as forms CS1, CS2, CS3, CS4 and CS5.

The major disadvantage with the above prior art process is the use of hazardous thionyl chloride may cause for many inconvenient reactions such as fire or explosion, irritation or toxic fumes in a fire, it produces lower yield and higher impurities. The complexity of the known processes for the preparation of the Canagliflozin and its intermediates are used expensive, corrosive/toxic reagents and drastic reactions conditions. The above process reagents or conditions are difficult to apply for industrially scale up.

SUMMARY OF THE INVENTION

The present invention provides a novel process for the preparation of Canagliflozin (I) and its hydrates thereof In one aspect of the present invention provides a novel process for the preparation of Canagliflozin (I), comprising the steps of;
 a) (5-bromo-2-methylphenyl) [5-(4-fluoro phenyl) thiophen-2-yl] methanone (IV) is reacted with tri alkyl orthoformate/trialkylorthoaceatate (XV), optionally in presence of acid to produce 2-[(5-bromo-2-methylphenyl)(dimethoxy)methyl]-5-(4-fluorophenyl)thiophene (XVI).
 b) the product of step a) is condensed with 2,3,5,6 tetrakis-O-trimethylsilyl-D-glucanolactone (VI) in presence of Grignard reagent (or) organo lithium reagents to produce dimethoxy-[5-(4-fluorophenyl)-thiophen-2-yl]-[2-methyl-5-(2-hydroxy-3,4,5 -trimethylsilyloxy-6-trimethylsilyloxymethyl-tetrahydropyran-2-yl)-pheny]-methane (XVII).

c) the product of step b) is deprotected in presence of acid and solvent to produce [5-(4-Fluoro-phenyl)-thiophen-2-yl]-[2-methyl-5-(3,4,5-trihydroxy-6-hydroxymethyl-2-methoxy-tetrahydro-pyran-2-yl)-phenyl]-methanone (VIII).
d) the product of step c) is reduced with trialkyl silane and lewis acid to produce Canagliflozin (I).
The process of the present invention schematically as shown in below:
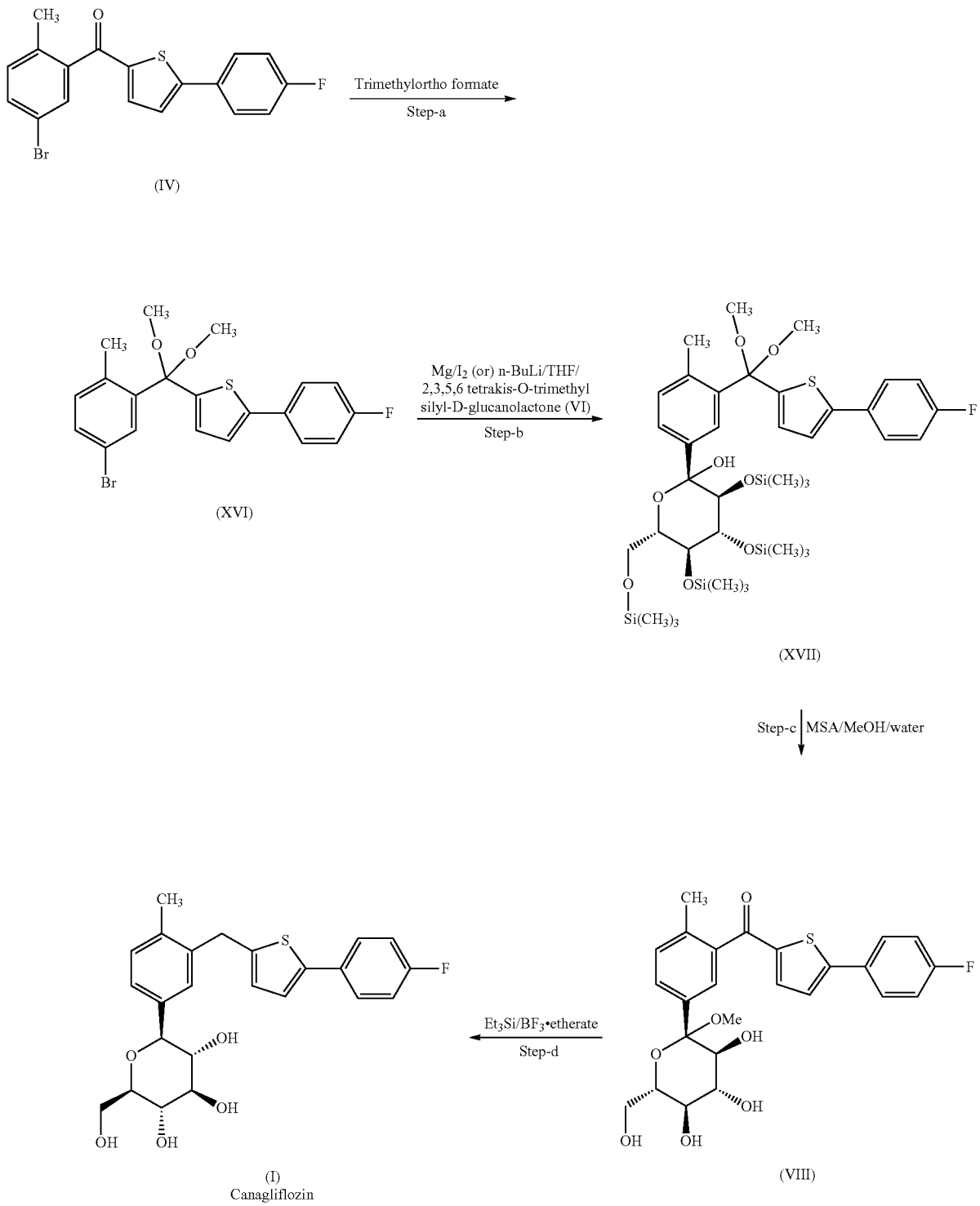

Another aspect of the present invention provides a process for the preparation of 2-[(5-bromo-2-methylphenyl)(dimethoxy)methyl]-5-(4-fluorophenyl)thiophene (XVI), comprising as follows (5-bromo-2-methylphenyl) [5-(4-fluoro phenyl) thiophen-2-yl] methanone (IV) is reacted with tri alkyl orthoformate/ tri alkyl orthoaceatate (XV), optionally in presence of acid to produce a novel intermediate of 2-[(5-bromo-2-methylphenyl)(dimethoxy)methyl]-5-(4-fluorophenyl)thiophene (XVI).

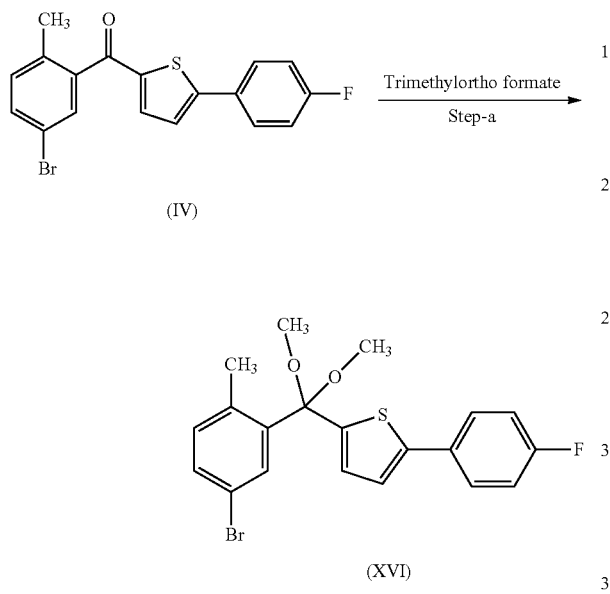

The other aspect of the above present invention provides a novel intermediate of 2-[(5-bromo-2-methylphenyl)(dimethoxy)methyl]-5-(4-fluorophenyl)thiophene (XVI)

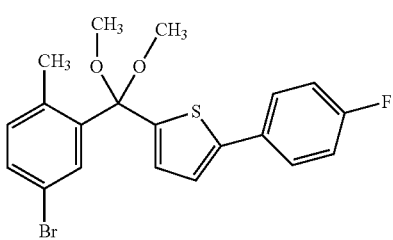

(XVI)

In yet another aspect of the present invention provides a process for the preparation of compound of formula (XVII), comprising as follows The compound of formula (XVI) is condensed with 2,3,5,6 tetrakis-O-trimethylsilyl-D-glucanolactone (VI) in presence of Grignard reagent (or) organo lithium reagents to produce a novel intermediate dimethoxy-[5-(4-fluorophenyl)-thiophen-2-yl ]-[2-methyl-5-(2-hydroxy-3,4,5-trimethylsilyloxy-6-trimethylsilyloxymethyl-tetrahydro-pyran-2-yl)-phenyl]-methane (XVII).

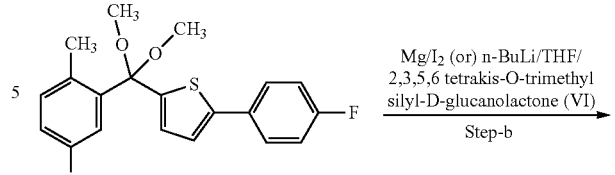

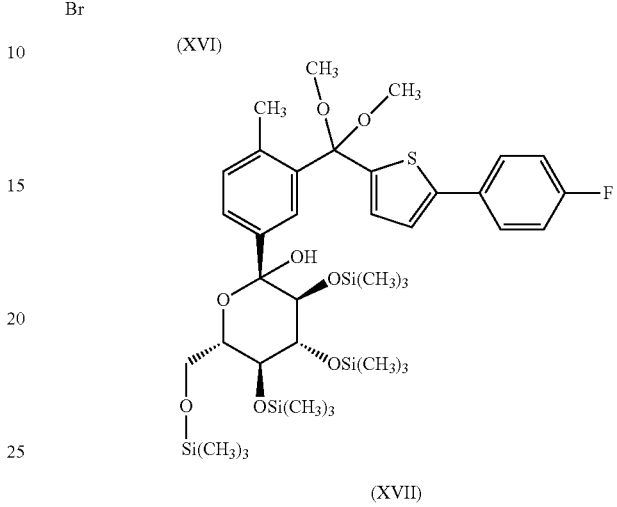

The other aspect of the above present invention provides a novel intermediate dimethoxy-[5-(4-fluorophenyl)-thiophen-2-yl]-[2-methyl-5-(2-hydroxy-3,4,5-trimethylsilyloxy-6-trimethylsilyloxymethyl-tetrahydro-pyran-2-yl)-phenyl]-methane (XVII).

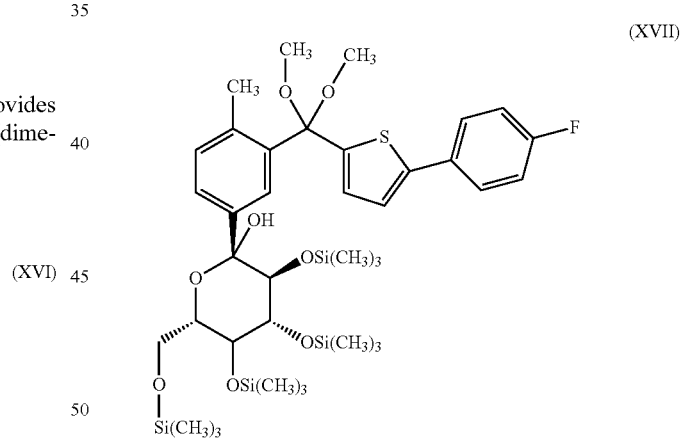

In another aspect of the present invention provides a process for the preparation of Crystalline form of Canagliflozin (I) hemi hydrate.

DETAILED DESCRIPTION OF THE INVENTION

The present invention provides a novel process for the preparation of Canagliflozin (I) or a pharmaceutically acceptable salts/hydrates thereof.

In one embodiment of the present invention relates to a novel process for the preparation of Canagliflozin (I), comprising the steps of;

a) (5-bromo-2-methylphenyl) [5-(4-fluoro phenyl) thiophen-2-yl] methanone (IV) is reacted with tri alkyl orthoformate/tri alkyl orthoaceatate (XV), optionally in presence of acid to produce 2-[(5-bromo-2-methylphenyl) (dimethoxy) methyl]-5-(4-fluorophenyl) thiophene (XVI).

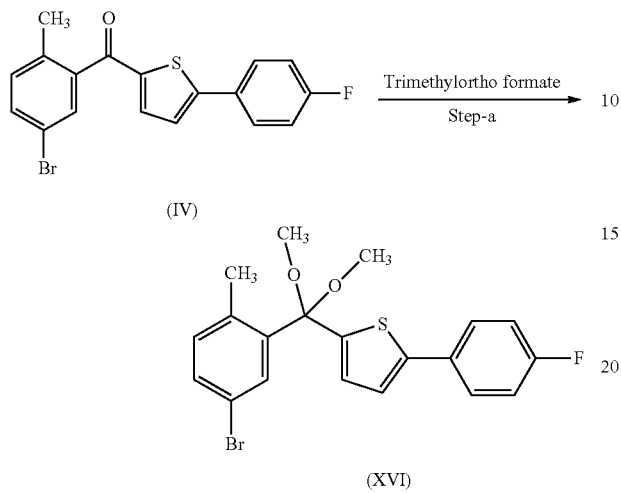

b) the product of step a) is condensed with 2,3,5,6 tetrakis-O-trimethylsilyl-D-glucanolactone (VI) in presence of Grignard reagent (or) organo lithium reagents to produce dimethoxy-[5-(4-fluorophenyl)-thiophen-2-yl]-[2-methyl-5-(2-hydroxy-3,4,5-trimethylsilyloxy-6-trimethylsilyloxymethyl-tetrahydropyran-2-yl)-phenyl]-methane (XVII).

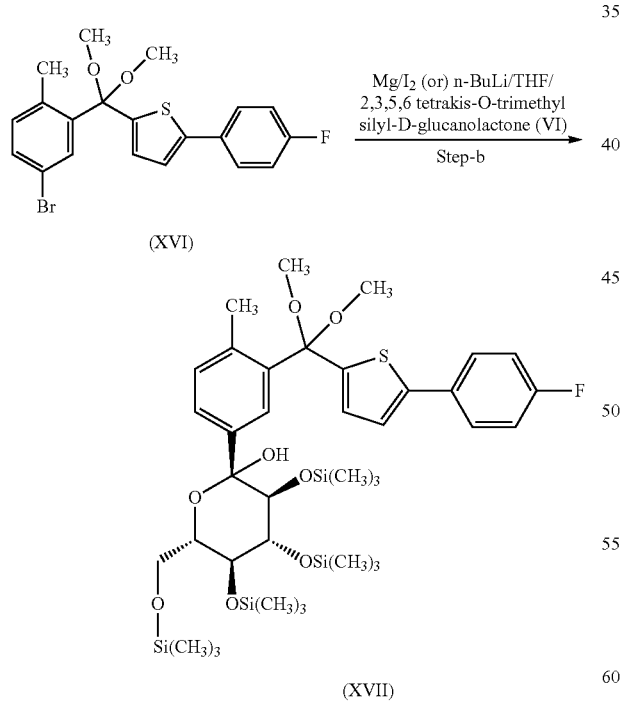

c) the product of step b) is deprotected in presence of acid and solvent to produce [5-(4-Fluoro-phenyl)-thiophen-2-yl]-[2-methyl-5-(3,4,5-trihydroxy-6-hydroxymethyl-2-methoxy-tetrahydro-pyran-2-yl)-phenyl]-methanone (VIII).

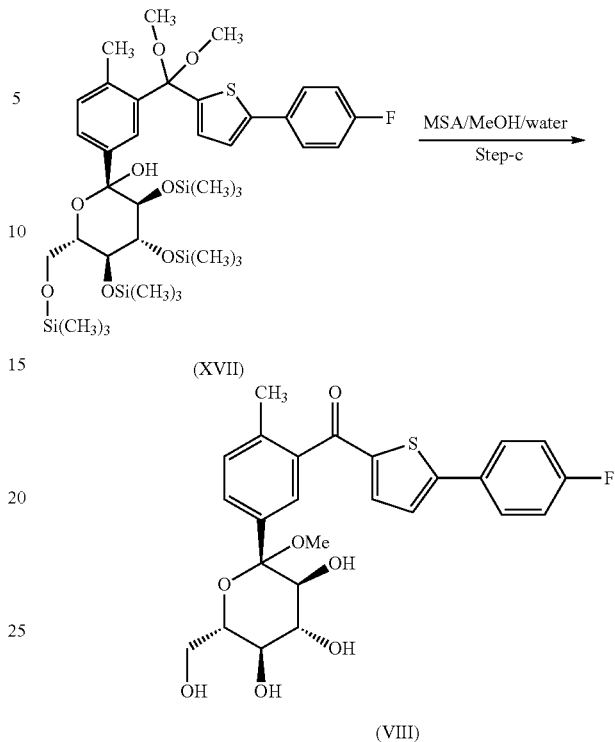

d) the product of step c) is reduced with trialkyl silane and lewis acid to produce Canagliflozin (I).

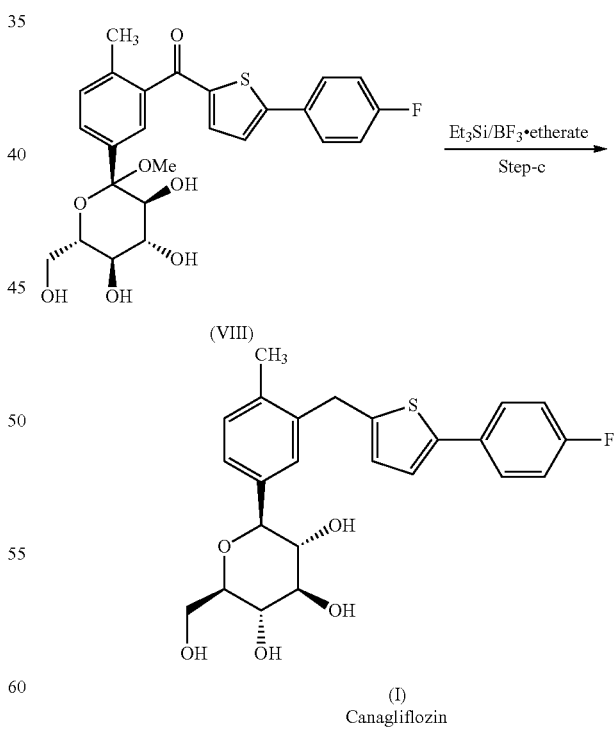

According to the embodiment of the present invention wherein, (5-bromo-2-methylphenyl) [5-(4-fluoro phenyl) thiophen-2-yl] methanone (IV) is reacted trialkyl orthoformate in presence of acid/alcohol solvent and followed by base/hydrocarbon solvent to produce 2-[(5-bromo-2-methylphenyl)(dimethoxy)methyl]-5-(4-fluorophenyl)thiophene (XVI); the compound of formula (XVI) is condensed with 2,3,5,6 tetrakis-O-trimethylsilyl-D-glucanolactone (VI) in presence of Grignard reagent (or) Organo lithium reagents in presence of solvent to produce hydroxy protected condensed product (XVII).

The compound of formula(XVII) is deprotected with mixture of acid/alcohol and followed by base to produce [5-(4-Fluoro-phenyl)-thiophen-2-yl]-[2-methyl-5-(3,4,5-trihydroxy-6-hydroxymethyl-2-methoxy-tetrahydro-pyran-2-yl)-phenyl]-methanone (VIII); further it is reduced with tri alkyl silane and Lewis acid complex in presence of solvent to produce Canagliflozin hemihydrates (I).

Another embodiment of the present invention provides a process for the preparation of 2-[(5-bromo-2-methylphenyl)(dimethoxy)methyl]-5-(4-fluorophenyl)thiophene (XVI), comprising as follows (5-bromo-2-methylphenyl) [5-(4-fluoro phenyl) thiophen-2-yl] methanone (IV) is reacted with tri alkyl orthoformate/tri alkyl orthoaceatate, optionally in presence of acid to produce a novel intermediate of 2-[(5-bromo-2-methylphenyl) (dimethoxy)methyl]-5-(4-fluorophenyl)thiophene (XVI).

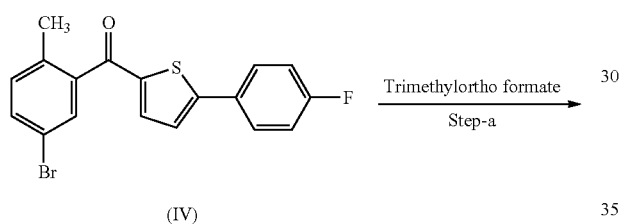

The other embodiment of the above present invention provides a novel intermediate of 2-[(5-bromo-2-methylphenyl)(dimethoxy)methyl]-5-(4-fluorophenyl)thiophene (XVI)

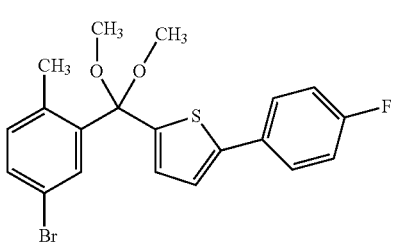

In yet another embodiment of the present invention provides a process for the preparation of compound of formula (XVII), comprising as follows The compound of formula (XVI) is condensed with 2,3,5,6 tetrakis-O-trimethylsilyl-D-glucanolactone (VI) in presence of Grignard reagent (or) organo lithium reagents to produce a novel intermediate dimethoxy-[5-(4-fluorophenyl)-thiophen-2-yl]-[2-methyl-5-(2-hydroxy-3,4,5-trimethylsilyloxy-6-trimethylsilyloxymethyl-tetrahydro-pyran-2-yl)-phenyl]-methane (XVII).

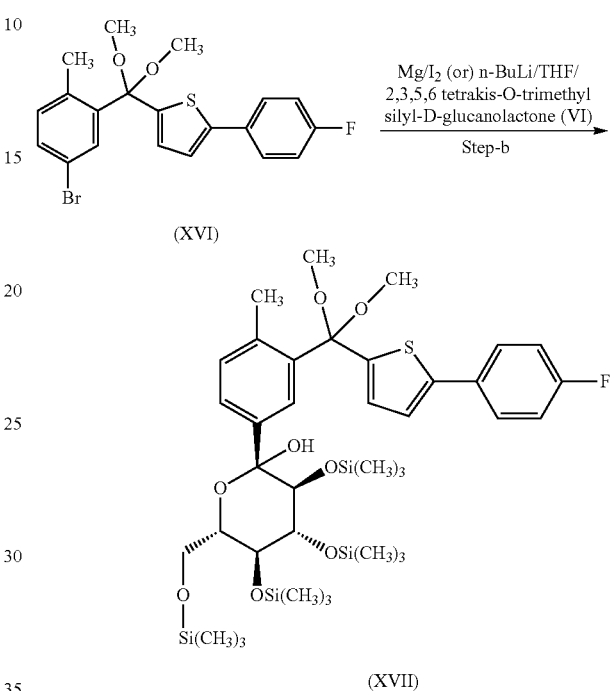

The other embodiment of the above present invention provides a novel intermediate of compound of formula (XVII).

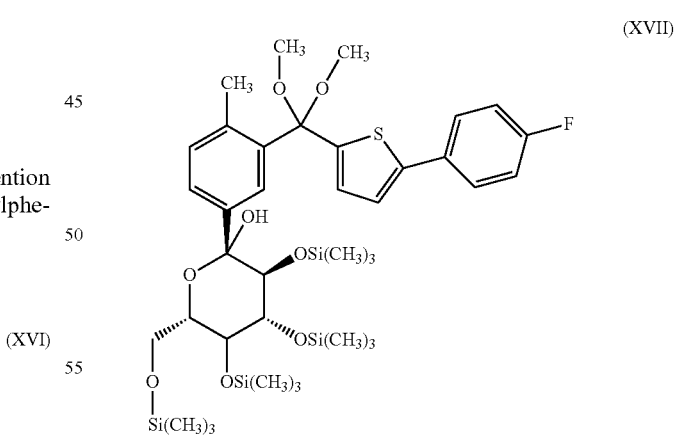

According to the embodiments of the present invention, the alky orthoformate/alkyl ortho acetate is selected form the group comprising of trimethyl orthoformate, triethyl orthoformate, triethyl ortho acetate, preferably trimethyl orthoformate; the acid is selected from group comprising hydrochloric acid, sulfuric acid, methane sulfonic acid, p-toluene sulfonic acid, preferably p-toluene sulfonic acid; the Grignard reagent is selected from group comprising alkyl magnesium halide; the halogen is selected from group comprising chlorine, fluorine, bromine, and iodine; the organic lithium reagent is selected from group comprising methyl lithium, sec-butyl lithium, iso propyl lithium, n-butyl lithium, t-butyl lithium and phenyl lithium, most preferably n-butyl lithium; the deprotecting agent is selected from group comprising, trifluoro acetic acid, hydrochloric acid, sulfuric acid, methane sulfonic acid, preferably methane sulfonic acid; the alcohol solvent is selected form the group comprising methanol, ethanol, propanol, butanol, isopropyl alcohol, preferably methanol; the reducing agent is selected form group comprising trimethyl silane, triethyl silane, tri isopropyl silane, preferably triethyl silane; the lewis acid is selected from group comprising boron trichloride, boron tribromide, diborane, boron trifluoride, and its complexes, preferably boron trifluoride diethyl etharate complex; and the solvent is selected from group comprising polar aprotic solvents such as dichloromethane, ethylacetate, tetrahydrofuran, acetonitrile etc; and polar protic solvents selected from group comprising water, methanol, the non polar solvent is selected from group comprising toluene, xylene, n-hexane, n-heptane, n-pentane etc; the base is selected from group comprising alkali metal bicarbonates such as sodium bicarbonate, potassium bicarbonate, lithium bicarbonate preferably sodium bicarbonate etc.

After the completion of reaction, the product may be isolated by filtration followed by washing with water (or) the solvent from the reaction may be removed using any suitable methods such as evaporation, atmospheric distillation or distillation under vacuum.

According to the present invention, the said methods should in particular be more industrially scalable, allow the desired compounds to be obtained with high yields, and use cheaper reagents which are simpler to handle and industrial applicable.

The process details of the invention are provided in the examples given below, which are provided by way of illustration only and therefore should not be construed to limit the scope of invention.

EXAMPLES

Example-1

Preparation of 2-[(5-bromo-2-methylphenyl)(dimethoxy)methyl]-5-(4-fluorophenyl)thiophene (XVI)

In a clean and dry four neck R.B flask fitted with mechanical stirrer, thermo-pocket and stopper charged trimethyl orthoformate (35.33 gm, 0.333 mole) and (5-bromo-2-methylphenyl)[5-(4-fluoro phenyl) thiophene-2-yl]methanone (IV) (50 gm, 0.133 mole) and stirred for 15 minutes at ambient temperature and the reaction mass was raised to 40-45° C., followed by slow addition of p-toluene sulfonic acid solution (1.5 gm PTSA dissolved in 50 ml methanol). The reaction mixture temperature was raised to 50-60° C. and stirred at same temperature till completion of reaction. The resultant mass was cooled to 25-30° C. and charge toluene (250 ml), stirs for 10-15 minutes, followed by addition of 5% sodium bicarbonate solution (250 ml) and stirred for 30 minutes to separate the organic layer. The organic layer was washed with purified water (2×200 ml), further the solvent was distilled under reduced pressure below 60° C. to obtain title compound 2-[(5-bromo-2-methylphenyl)(dimethoxy)methyl]-5-(4-fluorophenyl)thiophene (XVI).

Example 2

Preparation of [5-(4-Fluoro-phenyl)-thiophen-2-yl]-[2-methyl-5-(3, 4, 5-trihydroxy-6-hydroxy methyl-2-methoxy-tetrahydro-pyran-2-yl)-phenyl]-methanone (VIII).

In a clean and dry four neck R.B flask fitted with mechanical stirrer, thermo-pocket and stopper charged dry Tetrahydrofuran (200 ml), Magnesium turnings (3.43 g, 0.142 moles) and Iodine (0.2 g) under nitrogen atmosphere at 25-30° C. [Prepared a THF solution of [2-[(5-bromo-2-methylphenyl)(dimethoxy)methyl]-5-(4-fluorophenyl)thiophene] by dissolving (50 g, 0.118 mole) of compound of formula (XVI) in tetrahydrofuran (50 ml) in a separate flask]. The prepared ~10% THF solution was slowly added to above said Mg solution at 25-30° C. for 2-3 hours. After completion of addition, maintain the reaction mass was stirred at 30-35° C. for 2 hours to form Grignard reagent.

In a separate R B flask, 2,3,4,6 tetrakis-O-trimethylsilyl-D-Glucanolactone (49.87 gm, 0.106 moles) was dissolved in a dry Tetrahydrofuran (100 ml) under nitrogen atmosphere at 25-30° C., Cool the reaction mass to 0-5° C., followed by slow addition of above prepared Grignard reagent at same temperature, further it was stirred at 0-5° C. for 2 hours to complete the reaction. After completion, the reaction mass was quenched with mixture of methane sulfonic acid (25 gm) and methanol (400 ml) under cooling at 0-5° C., stirred for few hours at same temperature, further it was treated with 5% sodium bicarbonate solution (400 ml) and ethyl acetate (400 ml) to separate the layers. The organic layer was distilled out completely under reduced pressure at below 50° C.; the obtain residue is treated with mixture of toluene (100 ml) and hexane (400 ml) to get a title compound.

Example 3

Preparation of [5-(4-Fluoro-phenyl)-thiophene-2-yl]-[2-methyl-5-(3,4,5-trihydroxy-6-hydroxymethyl-2-methoxy-tetrahydro-pyran-2-yl)-phenyl]-methanone (VIII).

To a solution of [2-[(5-bromo-2-methylphenyl)(dimethoxy)methyl]-5-(4-fluorophenyl)) thiophene] (50 g, 0.1187 mole) in 400 ml tetrahydrofuran, slowly added n-Butyl lithium (110 ml, 1.6 molar in hexane) to a solution at −60° to −70° C. under nitrogen atmosphere. The reaction mass was stirred at same temperature for 30 minutes; further a solution of 2,3,4,6 tetrakis-O-trimethylsilyl-D-Gluconolactone (49.87 g, 0.106 moles) in toluene (400 ml) was slowly added to reaction mass at −60° to −70° C. The resultant mixture was stirred at same temperature conditions for 1-2 hrs, to till completion of reaction.

The reaction mass was quenched with ammonium chloride solution (400 ml), followed by addition of ethyl acetate (400 ml) to separate the layers. The organic layer was distilled out under reduced pressure till about half of the reaction mass. Further, the reaction mass was treated with methane sulfonic acid (30 g) and methanol (450 ml) and stirred at room temperature for 4-6 hours, followed by addition of 5% sodium bicarbonate solution (400 ml) and ethyl acetate (400 ml) to separate the layers. The organic layer was distilled out completely under reduced pressure at below 50° C.; the obtain residue is treated with mixture of toluene (100 ml) and hexane (400 ml) to get a title compound.

Example 4

Process for the Preparation of Canagliflozin Hemihydrate

In a clean and dry four neck R B Flask, charge acetonitrile (150 ml) and dichloromethane (150 ml) at room temperature, charge [5-(4-Fluoro-phenyl)-thiophen-2-yl]-[2-methyl-5-(3,4,5-trihydroxy-6-hydroxymethyl-2-methoxy-tetrahydro-pyran-2-yl)-phenyl]-methanone prepared in Example-2 or Example-3 (30 gm, 0.0614 moles). The reaction mass was cooled to 0-5° C. under nitrogen atmosphere, slowly added triethylsilane (18.2 gm, 0.246 moles) and stirred the reaction mass for 15 minutes at 0-5° C., followed by slowly addition of boron trifluoride diethyl etharate 46% solution (72.7 gm, 0.246 moles) at 0-5° C. and stirred for 30 minutes at same temperature. The resultant mixture was allowed to raise the temperature at 25-30° C. and stirred at same temperature for 3-5 hours till completion of reaction.

After completion, the reaction mixture was quenched with 5% sodium bicarbonate solution (300 ml) and stir for 15 minutes at 25-30° C. The organic layer was separated and washed with water, distilled out solvent under reduced pressure at below 50° C. to get a residue, further it was charge with ethyl acetate (150 ml), n-heptane (300 ml) and water (3 ml) and stirred for overnight at room temperature to form precipitated solid. The obtain solid was filtered and dried at 40-45° C. to get a title compound of Canagliflozin hemihydrate.

We claim:

1. A process for the preparation of canagliflozin comprising:
    a) reacting (5-bromo-2-methylphenyl) [5-(4-fluorophenyl) thiophen-2-yl] methanone with a tri alkyl orthoformate or tri alkyl orthoaceatate, optionally in the presence of acid, to produce 2-[(5-bromo-2-methylphenyl)(dimethoxy)methyl]-5-(4-fluorophenyl)thiophene;
    b) (i) reacting 2-[(5-bromo-2-methylphenyl)(dimethoxy) methyl]-5-(4-fluorophenyl)thiophene with magnesium and iodine at about 25° C. to about 30° C. to form a Grignard reagent, and (ii) condensing the resulting Grignard reagent with 2,3,5,6 tetrakis-O-trimethylsilyl-D-glucanolactone to produce dimethoxy-[5-(4-fluorophenyl)-thiophen-2-yl]-[2-methyl-5-(2-hydroxy-3,4,5-trimethylsilyloxy-6-trimethylsilyloxymethyl-tetrahydro-pyran-2-yl)-phenyl]-methane;
    c) deprotecting dimethoxy-[5-(4-fluorophenyl)-thiophen-2-yl]-[2-methyl-5-(2-hydroxy-3,4,5-trimethylsilyloxy-6-trimethylsilyloxymethyl-tetrahydro-pyran-2-yl)-phenyl]-methane in the presence of an acid and an alcohol solvent to produce [5-(4-fluorophenyl)-thiophen-2-yl]-[2-methyl-5-(3,4,5-trihydroxy-6-hydroxymethyl-2-methoxy-tetrahydro-pyran-2-yl)-phenyl]-methanone; and
    d) reducing [5-(4-fluorophenyl)-thiophen-2-yl]-[2-methyl-5-(3,4,5-trihydroxy-6-hydroxymethyl-2-methoxy-tetrahydro-pyran-2-yl)-phenyl]methanone with a trialkyl silane and a Lewis acid, wherein the Lewis acid is selected from boron trichloride, boron tribromide, diborane, boron trifluoride, and complexes thereof, to produce canagliflozin.

2. The process according to claim 1, wherein in step a) the tri alkyl orthoformate is selected from trimethyl orthoformate and triethyl orthoformate, the tri alkyl orthoaceatate is triethyl ortho acetate, and the acid is selected from hydrochloric acid, sulfuric acid, methane sulfonic acid, and p-toluene sulfonic acid.

3. The process according to claim 1, wherein in step c) the dimethoxy-[5-(4-fluorophenyl)-thiophen-2-yl]-[2-methyl-5-(2-hydroxy-3,4,5-trimethylsilyloxy-6-trimethylsilyloxymethyl-tetrahydro-pyran-2-yl)-phenyl]-methane is deprotected by reaction with a deprotecting agent in an alcohol solvent, where the deprotecting agent is selected from trifluoro acetic acid, hydrochloric acid, sulfuric acid, and methane sulfonic acid, and the alcohol solvent is selected from methanol, ethanol, propanol, and isopropyl alcohol.

4. The process according to claim 1, wherein in step d) the trialkyl silane is selected from trimethyl silane, triethyl silane, and tri isopropyl silane.

5. The process according to claim 1, wherein step d) is performed in a solvent selected from dichloromethane, ethyl acetate, tetrahydrofuran, acetonitrile, water, methanol, toluene, n-hexane, and any combination of any of the foregoing.

6. The process according to claim 1, wherein the Lewis acid in step d) is boron trifluoride diethyl etherate.

* * * * *